US008932641B2

(12) United States Patent
Nikaido et al.

(10) Patent No.: US 8,932,641 B2
(45) Date of Patent: *Jan. 13, 2015

(54) DRIED AMNION AND METHOD FOR DRYING TREATMENT OF AMNION

(75) Inventors: Toshio Nikaido, Toyama (JP); Toshiko Yoshida, Toyama (JP); Motonori Okabe, Toyama (JP); Ayaka Toda, Toyama (JP); Kiyotaka Kitagawa, Toyama (JP); Masahiko Arakawa, Chikuma (JP)

(73) Assignee: Amnos Co., Ltd., Toyama (JP)

( * ) Notice: Subject to any disclaimer, the term of this patent is extended or adjusted under 35 U.S.C. 154(b) by 1796 days.

This patent is subject to a terminal disclaimer.

(21) Appl. No.: 11/990,904

(22) PCT Filed: Aug. 18, 2006

(86) PCT No.: PCT/JP2006/316269
§ 371 (c)(1),
(2), (4) Date: Feb. 25, 2008

(87) PCT Pub. No.: WO2007/023750
PCT Pub. Date: Mar. 1, 2007

(65) Prior Publication Data
US 2009/0258082 A1    Oct. 15, 2009

(30) Foreign Application Priority Data

Aug. 26, 2005  (JP) ................................ 2005-245964
Aug. 10, 2006  (JP) ................................ 2006-218297

(51) Int. Cl.
| *A61K 35/50* | (2006.01) |
| *A61L 27/36* | (2006.01) |
| *A01N 1/02* | (2006.01) |
| *C12N 5/00* | (2006.01) |

(52) U.S. Cl.
CPC ............ *A61L 27/3641* (2013.01); *A61K 35/50* (2013.01); *A01N 1/02* (2013.01); *A01N 1/0205* (2013.01); *A01N 1/0289* (2013.01); *A61L 27/3604* (2013.01); *A61L 27/3683* (2013.01); *A61L 2430/40* (2013.01); *C12N 5/0068* (2013.01); *C12N 2533/92* (2013.01)
USPC ......................................... 424/522; 424/400

(58) Field of Classification Search
CPC ..................................................... A61K 35/50
USPC .................................................. 424/400, 522
See application file for complete search history.

(56) References Cited

U.S. PATENT DOCUMENTS

| 4,361,552 A * | 11/1982 | Baur, Jr. ........................ 424/582 |
| 6,152,142 A | 11/2000 | Tseng |
| 2003/0187515 A1 | 10/2003 | Hariri et al. |
| 2004/0126878 A1* | 7/2004 | Ramos et al. ................. 435/366 |
| 2006/0153928 A1* | 7/2006 | Kinoshita et al. ............. 424/582 |

FOREIGN PATENT DOCUMENTS

| JP | 2003-190192 A | | 7/2003 |
| JP | 2004-024852 A | | 1/2004 |
| WO | WO-03/043542 A1 | | 5/2003 |
| WO | WO-03/082201 A2 | | 10/2003 |
| WO | WO 2004/078225 | * | 9/2004 |
| WO | WO-2004/078225 A1 | | 9/2004 |
| WO | WO-2006/129673 A1 | | 12/2006 |

OTHER PUBLICATIONS

U.S. Appl. No. 12/528,103.*
Von Versen-Hoynick Frauke et al, "The influence of different preservation amd sterilisation steps on the histological properties of amnion allografts—light and scanning electron microscopic studies," Cell and Tissue Banking 2004, pp. 45-56, XP002544072, ISSN: 1389-9333.
Sippel et al., "Amniotic membrane surgery" Current Opinion Opthamology, 2001; 12:269-281.
Kruse et al.,"Cryopreserved human amniotic membrane:for ocular surface reconstruction", Grafe's Arch Clin Exp Opthamology (2000); 238:68-75.

* cited by examiner

*Primary Examiner* — Ruth Davis
(74) *Attorney, Agent, or Firm* — Birch, Stewart, Kolasch & Birch, LLP

(57)    ABSTRACT

The present invention provides a dried amnion which is dried with maintaining tissues of a raw amnion and can be easily stored for a prolonged period of time. An amnion which is dried with maintaining cells and tissues of a raw amnion can be produced by repeating a pressure-reducing operation and a pressure-recovery operation several times, the pressure-reducing operation comprising continuously heating a raw amnion placed in a treatment vessel by a far-infrared heater provided in the treatment vessel and reducing the pressure of the inside of the treatment vessel, and the pressure-recovery operation comprising recovering the reduced pressure of the inside of the treatment vessel with heating the amnion by microwaves irradiated from a microwave heating apparatus provided outside of the treatment vessel, and the amnion is characterized by retaining basement membranes and connective tissues which are constituents of the raw amnion.

4 Claims, 3 Drawing Sheets

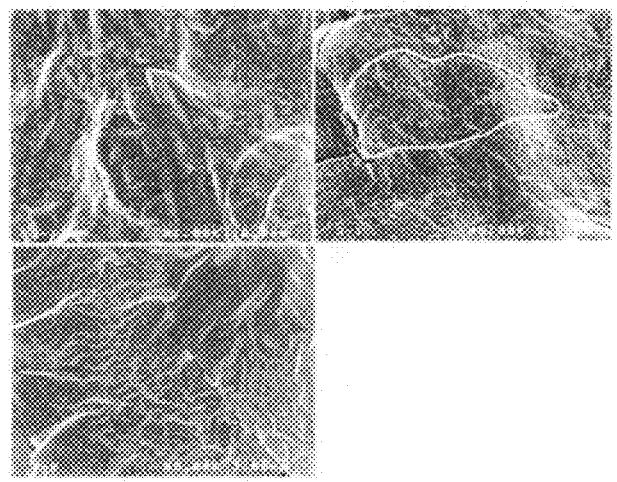
FIG. 3A  FIG. 3B
FIG. 3C
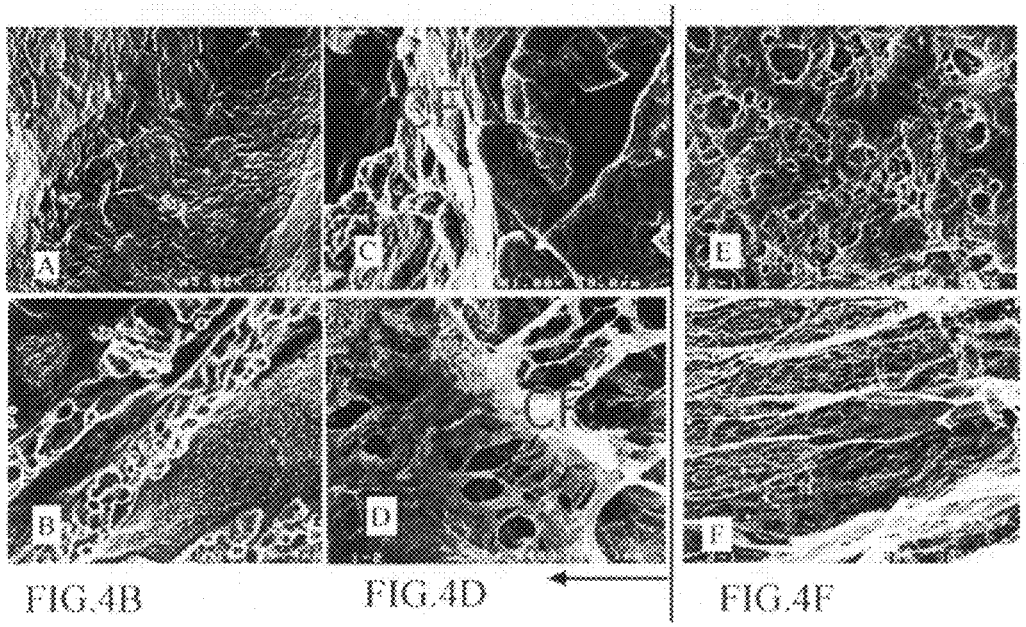
FIG. 4A  FIG. 4C  FIG. 4E
FIG. 4B  FIG. 4D  FIG. 4F
AMNION FREEZE-DRIED AFTER WASHING IN PHOSPHATE BUFFERED SALINE (PBS)
AMNION FREEZE-DRIED AFTER WASHING IN DISTILLED WATER

DRIED AMNION AND METHOD FOR DRYING TREATMENT OF AMNION

FIELD OF TECHNOLOGY

The present invention relates to a dried amnion and a method for a drying treatment of an amnion, more precisely relates to a dried amnion, which is produced by drying a raw amnion investing a human or an animal embryo, and a method for a drying treatment of the raw amnion.

BACKGROUND TECHNOLOGY

Conventionally, amnions have been used in medical operations for reconstructing surfaces of eyes (see Non-patent Document 1), and frozen human amnions, which are used for reconstructing surfaces of eyes, have been known (see Non-patent Document 2).

Corneal stem cells are seeded and cultured on amnions so as to produce corneal endothelium-like sheets, which are used for implanting corneal endothelium (see Patent Document 1).

Further, Patent Document 2 discloses a dried amnion including no epithelial layer, which is produced by removing an epithelial layer of an amnion except a part of a basement membrane and dehydrating by a vacuum-freeze drying method, the dried amnion can be stored in a container without contacting oxygen, and the dried amnion can be used for curing a corneal disease after soaking the dried amnion into a buffer solution, etc. so as to rehydrate it.

Non-patent Document 1: Curr. Opin. Ophthalmol., 2001; 12: 269-281

Non-patent Document 2: Graefe's Arch. Clin. Exp. Ophthalmol., 2000; 238: 68-75

Patent Document 1: Japanese Patent Kokai Gazette No. 2004-24852

Patent Document 2: WO2004/078225

DISCLOSURE OF THE INVENTION

Preferably, germfree raw amnions investing human or animal embryos, especially raw amnions of placentas obtained by cesarean birth are immediately used for treating eye diseases, etch.

However, suitable raw amnions cannot be always obtained, so it is necessary to preliminarily store suitable raw amnions.

In paragraphs 0026 and 0027 of Patent Document 1, a raw amnion is soaked into a preservation solution and cryopreserved at temperature of −80° C., and the frozen amnion is thawed at the room temperature when it is used. By the method, amnions can be easily stored.

However, a storage period of the frozen amnions is around three months, and they will be burned after going over the storage period.

When a raw amnion is frozen, if water in cells of the amnion is frozen and large ice crystals are formed, cell membranes will be broken, so the raw amnion must be frozen without forming large ice crystals in cells, and an operator must pay attention to a temperature falling rate for freezing the raw amnion.

As to the amnion cell destruction which occurs when the amnion is frozen, the similar problem occurs in the freeze dry method disclosed in Patent Document 2.

Further, a special facility is required so as to maintain the temperature of the frozen amnions at −80° C., so it is uneasy to store and transport the frozen amnions.

On the other hand, if dried amnions in which tissues of raw amnions can be retained are produced, it is easy to store and transport the dried amnions without paying special attention.

An object of the present invention is to provide a dried amnion, which is used for curing wounds and reconstructing a surface of an eye and which is capable of retaining tissues of a raw amnion and easily being stored for a long time, and a method for drying a raw amnion.

The inventors tried to freeze-dry a raw amnion so as to solve the above described problems and found that even if the dried amnion is dehydrated, cells of the dried amnion are significantly atrophied and the dehydrated amnion cannot be used for cell culture.

Thus, the inventors further studied the method for drying an amnion without breaking tissues of a raw amnion and found that an amnion can be dried with retaining tissues of a raw amnion by repeating a pressure-reducing operation and a pressure-recovery operation a plurality of times, the pressure-reducing operation comprising continuously heating a raw amnion placed in a treatment vessel by a far-infrared heater provided in the treatment vessel and reducing the pressure of the inside of the treatment vessel, and the pressure-recovery operation comprising recovering the reduced pressure of the inside of the treatment vessel with heating the amnion by microwaves irradiated from a microwave heating apparatus provided outside of the treatment vessel, so that the raw amnion can be dried with retaining cell tissues.

Namely, the dried amnion of the present invention, which is produced by drying a raw amnion investing a human or an animal embryo, is characterized in that the dried amnion is dehydrated so as to be stored in a sterilized dry atmosphere, and that epithelial cells, basement membranes and connective tissues, which are constituents of the raw amnion, are retained when the dried amnion is rehydrated in water or a buffer solution.

And, the method for a drying treatment of an amnion, which has invested a human or an animal embryo, is performed in a drying equipment including: means for reducing an inner pressure of a treatment vessel, in which the amnion is placed; means for heating the amnion, which is placed in the treatment vessel whose inner pressure has been reduced; and means for recovering the reduced inner pressure of the treatment vessel to the air pressure, and the method is characterized by alternately repeating a pressure-reducing operation and a pressure-recovery operation a plurality of times so as to dehydrate and dry the raw amnion placed in the treatment vessel, the pressure-reducing operation comprising the steps of: continuously heating the raw amnion placed in the treatment vessel with the heating means; maintaining the raw amnion at a prescribed temperature, at which basement membranes and connective tissues of the raw amnion are retained; and reducing the inner pressure of the treatment vessel with the pressure-reducing means, and the pressure-recovery operation comprising the step of: recovering the reduced inner pressure of the treatment vessel with the pressure-recovering means.

In the present invention, if the dried amnion derives from a human, the dried amnion can be suitably used for culturing sheet-shaped cells for regenerative medicine. By tightly sealing the dried amnion in a sterilized package, it can be stored for a long time.

The dried amnion can be suitably used as a medical material for reconstructing a surface of an eye or treating a wound.

The present invention further provides a method for using the dried amnion for reconstructing a surface of an eye and a method for reconstructing a surface of an eye with the dried amnion.

In the present invention, the heating means may include at least one of a far-infrared heater and a microwave irradiation apparatus. Far-infrared rays irradiated from the far-infrared heater and microwaves irradiated from the microwave irradiation apparatus are capable of heating the amnion placed in the reduced-pressure atmosphere. If a preset temperature of the heating means is 50° C. or lower, cell destruction of the amnion can be highly prevented.

Further, the raw amnion may derive from a human, and if the raw amnion is spread in the treatment vessel like a sheet, the raw amnion can be easily dehydrated.

If the pressure-recovering means recovers the inner pressure of the treatment vessel to a pressure lower than the air pressure, the inner pressure of the treatment vessel can be rapidly reduced to the lower limit pressure thereof in the next pressure-reducing operation.

Note that, if the drying method is terminated when the inner pressure of the treatment vessel in which the amnion is placed reaches the lower limit pressure of the treatment vessel in which no amnion is placed, the drying treatment can be uniformly terminated.

EFFECTS OF THE INVENTION

In the present invention, by reducing the inner pressure of the treatment vessel in which the raw amnion is placed, a boiling point of water in the raw amnion can be lowered. The raw amnion placed in the treatment vessel, whose inner pressure has been reduced, is heated by the heating means, so that water of the raw amnion can be evaporated and removed.

Note that, the water of the raw amnion placed in the treatment vessel, whose inner pressure has been reduced, is removed; if the raw amnion is heated by the heating means, the temperature of the raw amnion will be excessively increased until cell tissues thereof are destructed.

Thus, the reduced inner pressure of the treatment vessel is recovered to the air pressure so as to prevent the amnion from being excessively heated, and then the inner pressure of the treatment vessel is reduced again so as to evaporate the water of the raw amnion at the temperature of the heated amnion.

By alternately repeating the pressure-reducing operation and the pressure-recovery operation a plurality of times, the raw amnion, which is placed in the treatment vessel, can be dried without destructing its cells and tissues.

The dried amnion can be stored in the sterile dried air; and, in comparison with a freeze-dried amnion, much more storage stability and much more treatability of the dried amnion can be improved than freeze-dried amnion, and the dried amnion can be stored for a long time.

In the dried amnion, the cells and tissues of the raw amnion are retained without being destructed, the raw-like amnion can be produced by a rehydration process, in which the dried amnion is soaked into distilled water, a physiologic salt solution, an artificial aqueous fluid or a buffer solution, and the raw-like amnion can be used for culturing cells, curing a wound, reconstructing a surface of an eye, etc.

Note that, in case of using the dried amnion for curing a wound and reconstructing a surface of an eye, the dried amnion may be used without previously performing the rehydration process.

BRIEF DESCRIPTION OF THE DRAWINGS

FIGS. 3A-3C are scanning electron micrographs of a surface of the dried amnion.

FIGS. 4A-4F are scanning electron micrographs of a surface of a freeze-dried amnion.

OPTIMUM EMBODIMENTS OF THE INVENTION

Figure 1:
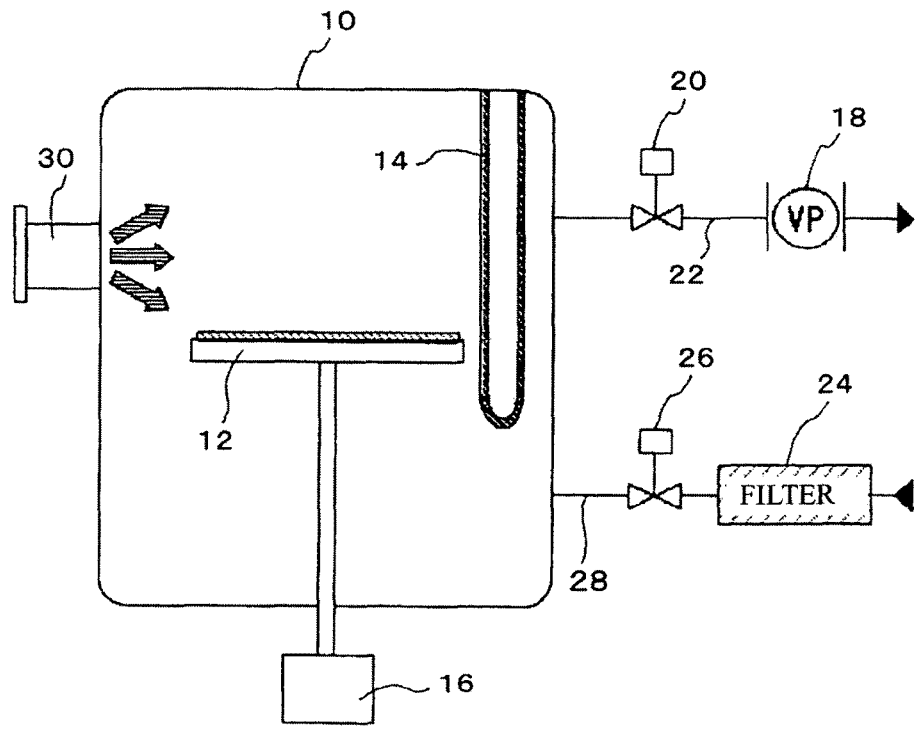
FIG. 1 is a schematic view of an example of an equipment for drying a raw amnion.

FIG. 1 is a schematic view of an example of an equipment for drying an amnion, in which the method of the present invention is performed. In the drying equipment shown in FIG. 1, a turn table 12 is provided in a treatment vessel 10, and the turn table 12 is turned by a motor 16, which is provided outside of the treatment vessel 10.

A vacuum pump 18, which acts as means for reducing an inner pressure of the treatment vessel 10, is provided outside of the treatment vessel 10, and an electromagnetic valve 20 is provided to a mid part of a pressure-reducing pipe 22, which is connected to the treatment vessel 10 and the vacuum pump 18.

A pressure-recovering pipe 28, which introduces outside air into the treatment vessel 10, whose inner pressure has been reduced, and which acts as means for recovering the inner pressure of the treatment vessel 10, is connected to the treatment vessel 10 and has a filter 24 for filtering the outside air and an electromagnetic valve 26.

A far-infrared heater 14 is provided in the treatment vessel 10 so as to heat an amnion mounted on the turn table 12 in the treatment vessel 10, and a microwave irradiation apparatus 30 is provided outside of the treatment vessel 10 so as to irradiate microwaves toward the amnion mounted on the turn table 12 in the treatment vessel 10, so the far-infrared heater and the microwave irradiation apparatus constitute means for heating the amnion. A preset temperature of the heating means is defined so as not to break cell tissues of the raw amnion, preferably the preset temperature is 50° C. or lower.

When a raw amnion is dried by the drying equipment shown in FIG. 1, a raw amnion, which has invested a human or an animal embryo, is mounted on the turn table 12. Preferably, a germfree raw amnion which has invested a human or animal embryo, especially a raw amnion of a placenta obtained by cesarean birth is used.

The raw amnion is spread like a sheet and mounted on the turn table 12 located in the treatment vessel 10. Preferably, the raw amnion is spread like a sheet and mounted on a piece of water-shedding paper, which is spread on the turn table 12 in the treatment vessel 10.

The turn table 12, on which the raw amnion has been mounted, is continuously turned by the motor 16, and the raw amnion is continuously heated by the heating means, i.e., the far-infrared heater 14.

While continuously heating the raw amnion placed in the treatment vessel 10 by the far-infrared heater 14, the vacuum pump 18, which acts as the pressure-reducing means, is driven and the electromagnetic valve 20 is opened so as to reduce the inner pressure of the treatment vessel 10. At that time, the electromagnetic valve 26 of the pressure-recovering means is closed.

When the inner pressure of the treatment vessel 10 is reduced, the boiling point of water is lowered, so that water in the raw amnion can be evaporated and removed at a prescribed temperature, at which cells and tissues of the raw amnion are not broken in the treatment vessel 10, e.g., 50° C. or lower.

Figure 2:
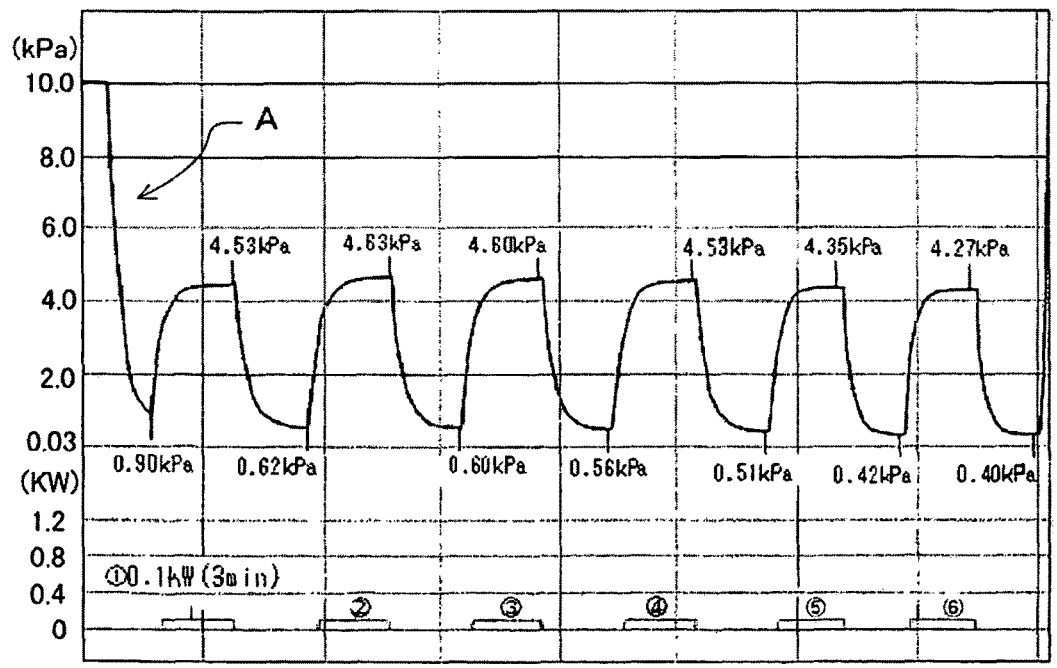
FIG. 2 is a graph showing time variation of an inner pressure of a treatment vessel of the drying equipment shown in FIG. 1, in which the raw amnion is placed.

A pressure reduction curve in the treatment vessel 10 is shown in FIG. 2. A horizontal axis of FIG. 2 indicates time; a vertical axis thereof indicates the inner pressure of the treatment vessel 10.

In FIG. 2, the pressure reduction curve A starts to reduce the inner pressure of the treatment vessel 10, in which the raw amnion is placed, from the air pressure. According to the pressure reduction curve A, a pressure reduction rate of the inner pressure of the treatment vessel 10 is high immediately after starting the pressure reduction; after a period time, pressure reduction rate of the inner pressure of the treatment vessel 10 is lowered. The reason is that the water in the amnion has been evaporated, and a temperature of the raw amnion is lowered by latent heat of the evaporation, so that evaporation rate of the water in the amnion is remarkably lowered.

In the drying equipment shown in FIG. 1, the temperature reduction of the amnion cannot be prevented by only far-infrared rays irradiated from the far-infrared heater 14, thus the microwave irradiation apparatus 30 irradiates microwaves toward the non-dried amnion, which has been mounted on the turn table 12, for a predetermined time so as to heat the amnion.

While irradiating the far-infrared rays and the microwaves, the vacuum pump 18 of the pressure-reducing means is stopped, the electromagnetic valve 20 is closed, and the electromagnetic valve 26 of the pressure-recovering means is opened so as to introduce outside air into the treatment vessel 10, so that the inner pressure of the treatment vessel 10 is recovered as shown by the pressure reduction curve A of FIG. 2. By recovering the inner pressure, overheating the raw amnion, which is caused by concentrating microwaves irradiated from the microwave irradiation apparatus 30, can be prevented.

The pressure-recovery operation is performed to prevent the overheat of the amnion, the inner pressure need not be recovered to the air pressure as shown by the pressure reduction curve A, so the recovered inner pressure may be lower than the air pressure as far as the amnion can be heated to the prescribed temperature. In this case too, cells and tissues of the amnion are not broken at the prescribed temperature.

Preferably, a suitable time for irradiating microwaves is determined by performing experiments.

After irradiating microwaves toward the amnion placed in the treatment vessel 10 for the prescribed time, the electromagnetic valve 26 of the pressure-recovering means is closed, the vacuum pump 18 of the pressure-reducing means is restarted, and the electromagnetic valve 20 is opened so as to produce the reduced-pressure atmosphere in the treatment vessel 10 and further evaporate and remove the water of the amnion at the temperature of the reheated amnion.

By alternately repeating the pressure-reducing operation, in which the inner pressure of the treatment vessel 10 is reduced with irradiating far-infrared rays toward the amnion, and the pressure-recovery operation, in which the inner pressure of the treatment vessel 10 is recovered with irradiating far-infrared rays and microwaves toward the amnion, as shown in FIG. 2, the raw amnion placed in the treatment vessel 10 can be dried without breaking cells and tissues thereof.

With the progress of the drying process, the inner pressure of the treatment vessel 10 in which the amnion is placed is reduced and approached to a lower limit pressure of the treatment vessel 10 in which no amnion is placed. When the inner pressure of the treatment vessel 10 in which the amnion is placed reaches the lower limit pressure of the treatment vessel 10 in which no amnion is placed, we can empirically judge that the drying process has terminated. By judging the termination of the drying process on the basis of the lower limit pressure, amnions can be uniformly dried.

The dried amnion can be stored in sterile dried air, for example it may be sealed and stored in a sterilized package in which a drying agent is provided. Under a suitable condition, the dried amnion can be stored for one year or more.

Note that, the drying equipment shown in FIG. 1 has the far-infrared heater 14 and the microwave irradiation apparatus 30 as the heating means; if one of the far-infrared heater 14 and the microwave irradiation apparatus 30 has enough power, one of them may be employed as the heating means.

FIG. 3 shows scanning electron micrographs of the surface of the amnion dried by the drying equipment shown in FIG. 1. FIGS. 3A-3C are scanning electron micrographs of different parts of the surface of the amnion, and the surface is formed flat, without asperities and fractures, and has a uniform structure. In FIG. 3B, a part enclosed by a solid line is a cell, and scaly cells are observed.

Note that, in FIGS. 3A and 3B which show the opposite side of FIG. 3B, no clear structure is observed because connective tissues including stromal elements under epithelium are fully retained, we think.

On the other hand, FIG. 4 shows scanning electron micrographs of surfaces of freeze-dried amnions. FIGS. 4A-4D show a freeze-dried amnion produced by washing a raw amnion in a phosphate buffered saline (PBS) and freezing and storing the washed amnion; FIGS. 4A and 4B show one side face of the dried amnion(epithelium); FIGS. 4C and 4D show the opposite side face thereof.

In FIGS. 4A and 4B, cells are arranged like scales, but they cannot be distinguished due to many wrinkles.

In FIGS. 4C and 4D, collagen fibers (CF) are observed like a sheet.

FIGS. 4E and 4F show a freeze-dried amnion produced by washing a raw amnion in distilled water and freeze-drying the washed amnion; FIG. 4E show one side face of the dried amnion(epithelium); FIG. 4F show the opposite side face thereof in it.

In FIG. 4E, large holes and small holes formed in cells are observed; in FIG. 4F, cytoplasm of cells and all stromal elements are washed away, but collagen fibers only exist.

Unlike the dried amnion produced by drying a raw amnion with the drying equipment shown in FIG. 1, an epithelium and connective tissues of the freeze-dried amnion cannot be stored perfectly.

Figures 5A, 5C:
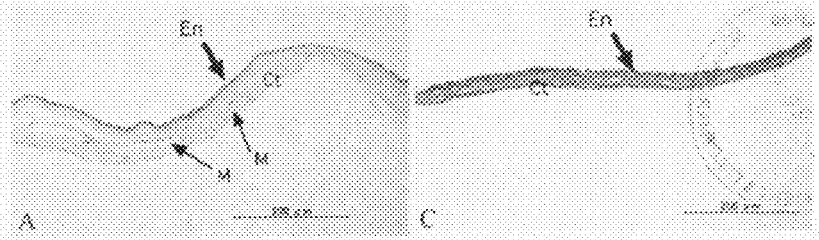
FIGS. 5A-5D are scanning electron micrographs of an amnion, which is obtained by rehydrating a dried amnion in a phosphate buffered saline (PBS), and a raw amnion.

FIG. 5A is a micrograph of an amnion, which was produced by drying a raw amnion with the drying equipment shown in FIG. 1 and soaking the dried amnion into a phosphate buffered saline (PBS) so as to rehydrate the amnion. The rehydrated amnion, which was produced by rehydrating the dried amnion in the phosphoric phosphate buffered saline (PBS), was formed into a specimen sample, by an ordinary microscopic specimen production method, and tissue images were shot through an optical microscope. The specimen sample was produced by the steps of: fixing the rehydrated amnion in a 10% formalin fixing solution; performing alcoholic dehydration; performing xylene penetration; performing paraffin embedding; slicing the paraffin-embedded amnion to form into the specimen sample having a thickness of 1-2 μm; and staining the sliced specimen sample by a hematoxylin-eosin stain (H-E stain) method.

Figures 5B, 5D:
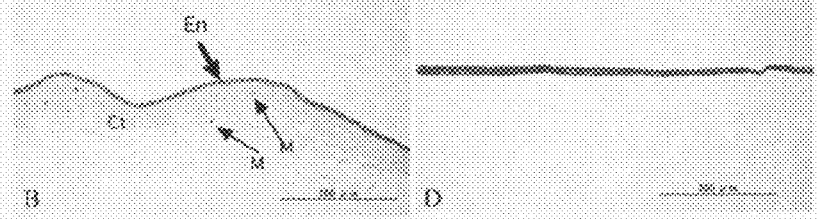

For reference, a micrograph of a raw amnion is shown in FIG. 5D. The micrograph was shot as well as the micrograph shown in FIG. 5A.

According to FIGS. 5A and 5D, epithelial cells (En), connective tissues (Ct) and mesenchymal cells (indicated by arrows M) are observed in the both micrographs, and the both have similar tissue images.

On the other hand, FIGS. 5C-5D show tissue images of dried amnions, which were produced by freeze-drying raw amnions. The micrographs were shot as well as the micrograph shown in FIG. 5A. The amnion shown in FIG. 5C was produced by washing a raw amnion in distilled water, freeze-drying the washed amnion and rehydrating the dried amnion in a phosphate buffered saline (PBS). The amnion shown in FIG. 5D was produced by freeze-drying a raw amnion and rehydrating the dried amnion in a phosphate buffered saline (PBS).

In comparison with FIGS. 5A-5B, the tissue shown in FIG. 5C is remarkably atrophied, an epithelial cell (En) is concentrated and few cells are observed in connective tissues. In comparison with FIG. 5C, the cell shown in FIG. 5D is further atrophied.

The dried amnion shown in FIGS. 3A-3C can be suitably used as a medical material for reconstructing a surface of an eye or curing a wound. In this case, the dried amnion may be cut to a proper size and adhered onto an affected part, the dried amnion may be used to coat a wound, the dried amnion may be implanted in a body or filled in a defective part. The dried amnion may be rehydrated in distilled water, a physiologic salt solution, an artificial aqueous fluid or a buffer solution before using.

The dried amnion may be used as a medical material for reconstructing a surface of an eye, for example it can be used for: supporting formation of conjunctival bleb and suppressing scar, which relate to an operation for glaucoma; accelerating regeneration of corneal epithelial cells and preventing leakage of an eye chamber aqueous fluid from a defective part, which relate to corneal ulcer; preventing angiogenesis and a rejection response, which relates to corneal transplant; and filling a defective part of conjunctiva, which is formed after removing pterygium tissues.

EXPERIMENT 1

(1) Obtaining Raw Amnion

Serosal membranes and blood coagulum were immediately washed and removed from a placenta, which had been obtained from an assented pregnant woman by cesarean birth, in a sterile physiologic salt solution so as to obtain a raw amnion. The raw amnion was sealed in a spitz (sterilized test tube), together with the physiologic salt solution, and refrigerated.

(2) Drying Raw Amnion

The raw amnion was dried by the drying equipment shown in FIG. 1. In the drying equipment, a magnetron having output power of 1.5 KW was used as the microwave irradiation apparatus 30. The preset temperature of the far-infrared heater 14 was 50° C., and far-infrared rays are continuously irradiated toward the amnion from starting the drying process until terminating the drying process. Further, the lower limit pressure of the treatment vessel 10 with no amnion was preset to 0.4 kPa by the vacuum pump 18.

To dry the raw amnion with the drying equipment shown in FIG. 1, the raw amnion (50 g) was taken out from the spitz (sterillized test tube) and spread on cooking paper, which acted as the water-absorbing paper and which had been spread so as not form wrinkles in the raw amnion, and then the raw amnion was mounted onto a tray. The tray was mounted onto the turn table 12 placed in the treatment vessel 10, and then the turn table 12 was turned. The turn table 12 was continuously turned from starting the drying process until terminating the drying process.

Next, the far-infrared heater 14 was turned on, the vacuum pump 18 was driven and the electromagnetic valve 20 was opened so as to reduce the inner pressure of the treatment vessel 10. After a period time from starting the drying process, a pressure reduction rate was lowered; when the inner pressure reached 0.90 kPa, the vacuum pump 18 was stopped, the electromagnetic valve 20 was closed and the electromagnetic valve 26 was opened so as to perform the pressure-recovery operation, wherein air from which dusts and bacteria had been removed by the filter 24 was introduced into the treatment vessel 10, until the inner pressure of the treatment vessel 10 reached 4.53 kPa.

When the pressure-recovery operation was started, the magnetron, which acted as the microwave irradiation apparatus 30, was turned on so as to irradiate microwaves toward the amnion mounted on the turn table 12.

After heating the amnion, by the far-infrared heater 14 and the magnetron, for three minutes, the magnetron was turned off, and then the pressure-reducing operation was restarted with turning on the far-infrared heater 14. After the inner pressure of the treatment vessel 10 reached 0.62 kPa, the pressure-recovery operation for recovering the inner pressure of the treatment vessel 10 to 4.63 kPa and the heating operation for heating the amnion for three minutes, by the far-infrared heater 14 and the magnetron, were performed. The pressure-reducing operation, the heating operation and the pressure-recovery operation were repeated six times until terminating the drying process of the amnion.

The termination of the drying process was judged on the basis of: the lower limit pressure of the treatment vessel 10 of the fifth pressure-reducing operation; and the lower limit pressure of the treatment vessel in which no amnion was placed. Namely, when the lower limit pressure of the sixth pressure-reducing operation reached 0.40 kPa, which was equal to the lower limit pressure of the treatment vessel in which no amnion was placed, the termination of the drying process was judged.

The raw amnion placed in the treatment vessel 10 was 50 g; on the other hand, the dehydrated and dried amnion was 1 g, and it was sealed in a sterilized package, together with a drying agent, for storage.

(3) Condition of Dried Amnion

The surface of the dried amnion was observed by a scanning electron microscope, so that the surface was formed flat, without asperities and fractures, and had a uniform structure as shown in FIGS. 3A-3C.

The dried amnion was rehydrated in a phosphate buffered saline (PBS) and formed into a specimen sample, by an ordinary microscopic specimen production method, and the specimen sample was observed by an optical microscope, so that epithelial cells (En), connective tissues (Ct) and mesenchymal cells (indicated by arrows M) were observed, as shown in FIG. 5A, as well as the raw amnion.

EXPERIMENT 2

The dried amnions produced by Experiment 1 were used for defective recovery.

(1) Forming and Curing Deficiency

Hairs of back parts of seven mice (C5γBL/6♂; weight 42-46 g) were removed, and then four circular defective wounds were formed in the hair-removed part of each mouse by a trephine having a diameter of 3 mm. Each of the wounds reached hypodermal tissues, dermis was perfectly disappeared, and degrees of the wounds were Stage II to stage III of Shea classification and NPUAP (National Pressure Ulcer Advisory Panel) classification.

For each mouse, one of the four defective wounds was coated with the dried amnion, which was adhered on a film (a dressing agent); another wound was coated with gauze including a hemostatic agent, which was adhered on a film (a dressing agent). One of the rest two wounds was coated with a film (a dressing agent) only; the other wound was not coated.

The dried amnion was produced by Experiment 1, sealed in the sterilize package together with the drying agent and stored for one month, and the amnion was used in the dry state.

As to materials coating the defective wounds, all of the materials coating the wounds were well adhered. Especially, the dried amnion was flat and has high adhesiveness, so that the dried amnion easily adhered and perfectly coated the entire wound.

After a lapse of seven days from starting the cure, the materials were removed so as to observe cure processes.

Note that, the coating materials were not exchanged during the processes, and in case that the coating materials were lost, the wounds were left as they were.

(2) Visual Observation and Palpation

By visual observation, the wounds coated with the materials, i.e., the dried amnion, the gauze including the hemostatic agent and the film only, were steadily cured.

However, in case of coating with the gauze including the hemostatic agent and the film only, there were significant differences of the cure processes between the wounds; some wound emitted blood after a lapse of seven days, on the other hand some wounds were completely cured. Further, abraded wounds were newly formed in peripheral parts of some defective wounds, in which the film and the gauze were adhered, due to itching paraesthesia.

On the other hand, in all of the wounds coated with the dried amnions, sizes of opening sections of the wounds were reduced.

Figure 6:
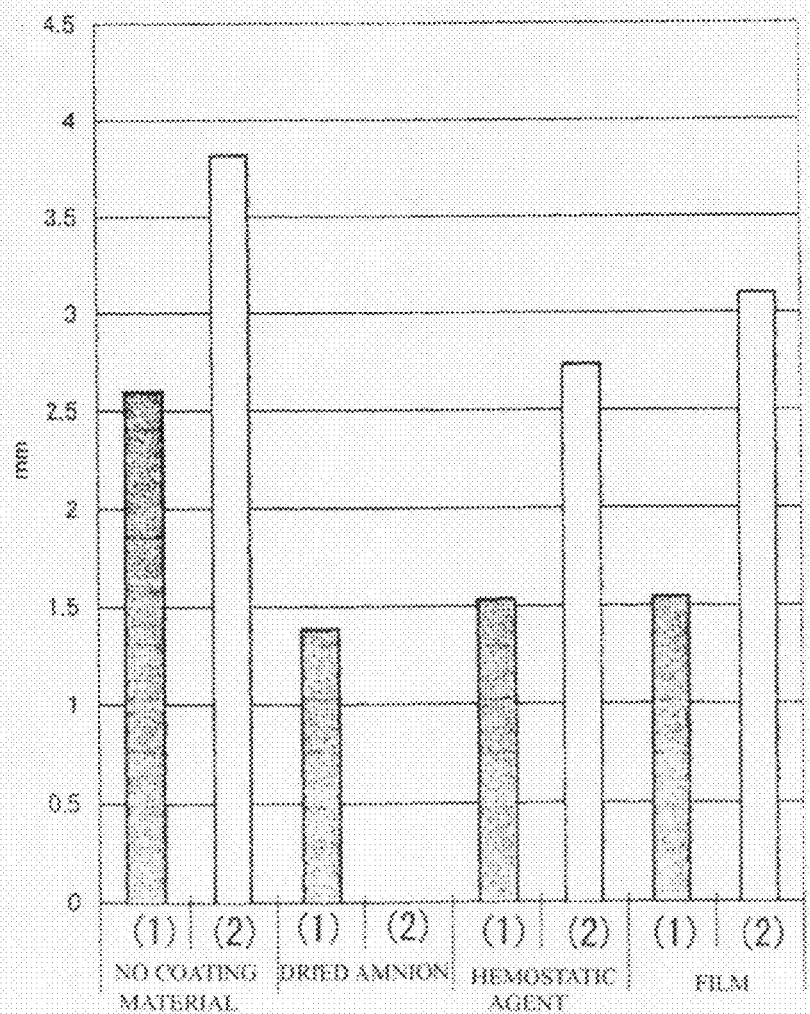
FIG. 6 is a graph showing progresses of curing defective wound area.

Next, diameters of the opening sections and extents of indurated areas of the wounds were measured, and the results are shown in FIG. 6. In FIG. 6, the diameters of the opening sections are (1); the extents of the indurated areas are (2).

According to FIG. 6, the diameters of the opening sections of the wounds coated with the dried amnions, the gauze including the hemostatic agent and only the films were smaller than those of the non-coated wounds.

By palpating the wounds, indurated parts, each of which encircles the opening section, were detected in the non-coated wounds and the wounds coated with the gauze including the hemostatic agent and only the films.

On the other hand, no indurated parts were detected in all of the wounds coated with the dried amnions by palpation.

In comparison with the gauze including the hemostatic agent, the adhesiveness of the dried amnion to the wound was higher, the dried amnion less stimulated the wounds, and the dried amnion restrained scar formation and excessive tissue atrophy.

EXPERIMENT 3

The dried amnions produced by Experiment 1 were used for curing following eye diseases.

(1) Further Operation Performed after Operation for Glaucoma and Leakage from Conjunctival Bleb A dried amnion was rehydrated in a physiologic salt solution and embedded under a reconstructed scleral flap of conjunctival bleb.

To prevent leakage from the conjunctival bleb, the amnion rehydrated in the physiologic salt solution was adhered by a cyanoacrylate bioadhesive.

As the result of the treatment, hypotonia bulbi was observed, and scar formation in conjunctiva was restrained. The adhered amnion was peeled off next day, and the wound was cured naturally.

(2) Corneal Perforation Caused by Corneal Ulcer

A dried amnion was adhered by a cyanoacrylate bioadhesive. As the result of the treatment, the perforation was coated with the amnion and cured.

(3) Pterygium

Pterygium tissues were cut and removed, and a rehydrated amnion, which had been produced by rehydrating a dried amnion in a physiologic salt solution, was stitched with the defected part of conjunctiva. As the result of the treatment, the amnion engrafted to the defected part.

Industrial Applicability

In the present invention, the dried amnion can be stored in sterile dried air for a long time, and basement membrane and connective tissues of the raw amnion are retained when the dried amnion is rehydrated in distilled water, a physiologic salt solution, an artificial aqueous fluid or a buffer solution.

In case of rehydrating the dried amnion in water or a buffer solution, the amnion can be brought back to the condition immediately after obtaining, and it can be used for culturing cells, curing a wound, reconstructing a surface of an eye, etc.

Further, the dried amnion can be suitably used as a medical material for reconstructing a surface of an eye or curing a wound.

What is claimed is:

1. A dried amnion being produced by a production method comprising the steps of:
    placing a raw amnion of a human or an animal in a treatment vessel; and
    performing a pressure-reducing operation in the treatment vessel while an inside of the treatment vessel is heated and has a reduced inner air pressure,
    then performing a pressure-recovery operation in the treatment vessel while the inside of the treatment vessel is heated and has an inner air pressure that is recovered to a level that occurred prior to performing the pressure-reducing operation, and
    then repeating a sequence of the pressure-reducing operation followed by the pressure-recovery operation a plurality of times,
    thereby dehydrating the raw amnion and producing the dried amnion,
    wherein cellular tissues of the dried amnion are retained without being substantially broken, so that the dried amnion is storable in a sterilized dry atmosphere, and
    epithelium cells, basement membranes and connective tissues which are constituents of the raw amnion are retained when the dried amnion is rehydrated in water or a buffer solution.

2. The dried amnion according to claim 1, wherein the dried amnion is tightly sealed in a sterilized package.

3. The dried amnion according to claim 1, wherein the dried amnion is a medical material for reconstructing a surface of an eye.

4. The dried amnion according to claim 1, wherein the dried amnion is a medical material for treating a wound.

* * * * *